United States Patent [19]

Morong, III

[11] 4,395,647

[45] Jul. 26, 1983

[54] HALF-WAVE SIGNAL ISOLATOR WITH MEANS FOR CONTROLLING FLUX IN THE COUPLING TRANSFORMER

[75] Inventor: William H. Morong, III, Newton, Mass.

[73] Assignee: Analog Devices, Incorporated, Norwood, Mass.

[21] Appl. No.: 203,451

[22] Filed: Nov. 3, 1980

[51] Int. Cl.³ .............................................. H03K 5/08
[52] U.S. Cl. .................................. 307/540; 307/261; 330/10; 328/170
[58] Field of Search .................... 328/170, 221; 330/8, 330/10; 323/356, 201, 245; 307/260, 261, 259, 269; 332/47

[56] References Cited

U.S. PATENT DOCUMENTS

| | | | |
|---|---|---|---|
| 2,057,998 | 10/1936 | Bohm | 328/221 |
| 3,229,122 | 1/1966 | Engle | 330/10 |
| 4,066,974 | 1/1978 | Reinhard | 330/10 |

Primary Examiner—Stanley D. Miller
Assistant Examiner—B. P. Davis
Attorney, Agent, or Firm—Parmelee, Bollinger & Bramblett

[57] ABSTRACT

A signal isolator including a coupling transformer with modulate/demodulate switches in series with the primary and secondary windings. The switches are driven in synchronism by an oscillator. Resonating capacitors are connected in parallel with the transformer windings to form an LC tank circuit tuned approximately to the operating frequency of the switch-drive oscillator. When the switches are closed, the current in the transformer windings ramps in a linear fashion in response to application of the input voltage, and when the switches are opened, the current varies in a cosine curve to provide smooth transitions at both ends to the ramp current, thus controlling the flux in the transformer core so as to minimize instability effects.

6 Claims, 5 Drawing Figures

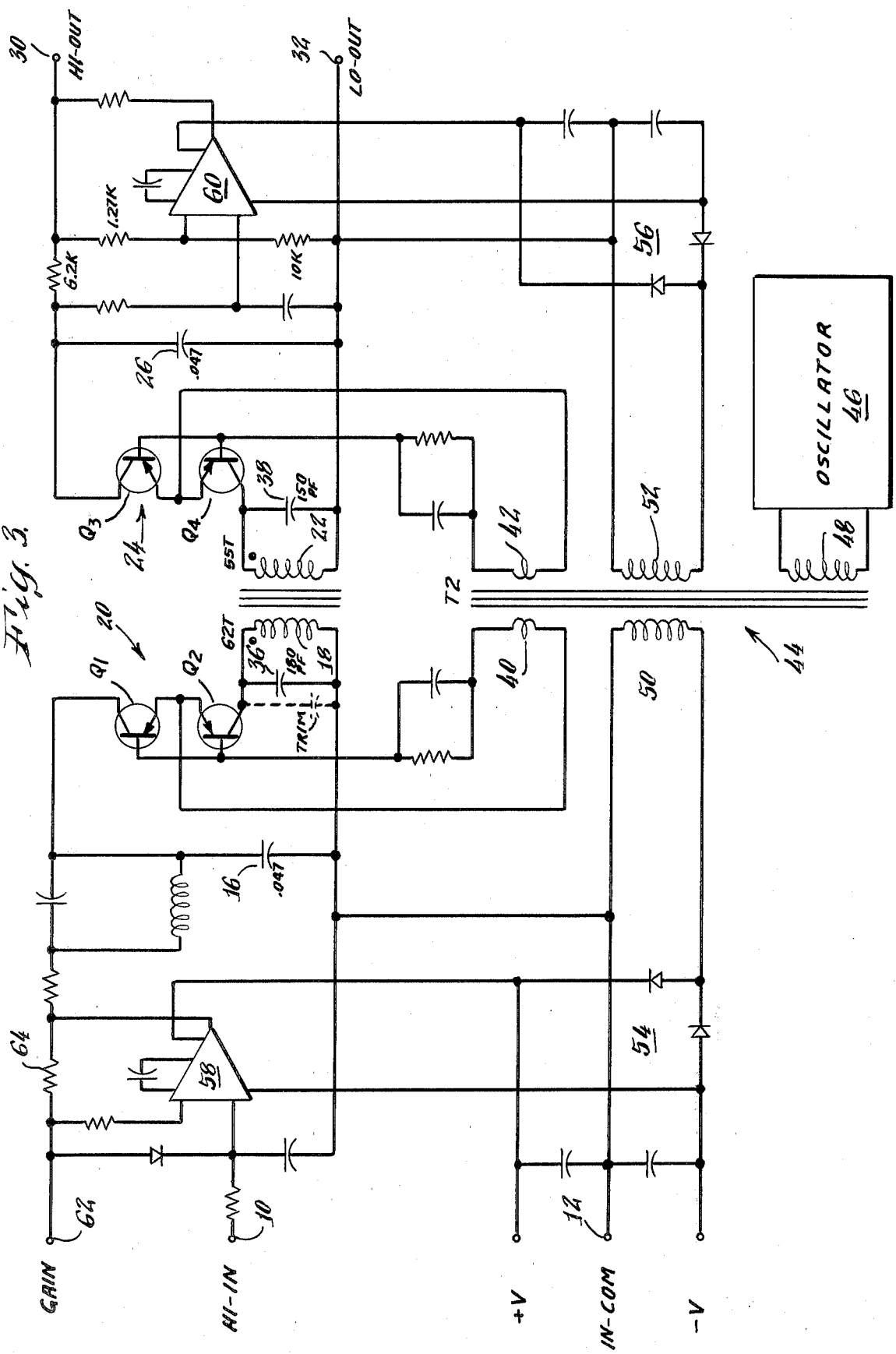

HALF-WAVE SIGNAL ISOLATOR WITH MEANS FOR CONTROLLING FLUX IN THE COUPLING TRANSFORMER

BACKGROUND OF THE INVENTION

1. Field of the Invention

This invention relates to electrical signal isolators for translating a signal level without establishing any conductive connection between input and output. More particularly, this invention relates to half-wave transformer-coupled isolators.

2. Description of the Prior Art

Electrical signal isolators are used in a wide variety of electrical systems, to enable signal levels to be translated from one part of a system to another without permitting the flow of direct current therebetween. Isolators are used in diverse applications such as industrial process control systems, making medical measurements of the human body, and so on.

A number of different types of isolators have been used in the past. Many isolators employ transformer coupling to establish a signal path without DC conductivity. Reference in that regard may be made to U.S. Pat. Nos. 3,946,324 (L. R. Smith), 4,054,829 (T. J. Searle), and 4,066,974 (C. J. Reinhard) simply as illustrative of different kinds of isolators; many other kinds of transformer-coupled isolators are described in still other patents and publications.

One type of transformer-coupled isolator which has significant advantages is that referred to as a half-wave isolator. In such an arrangement, a d-c (or slowly varying) input signal is modulated (chopped) by an electronic switch connected in series with the transformer primary. The switch is driven, typically by an oscillator carrier signal, so as to close the series circuit to the transformer primary on alternate half-cycles. A corresponding demodulator switch is employed in series with the transformer secondary winding to recover a signal corresponding to the original d-c signal. The demodulator switch is driven by the same oscillator signal as the modulator switch, so as to establish synchronism between the two switches.

Such half-wave signal isolators have been used extensively heretofore. However, prior isolators of that type have suffered from certain serious problems which have made such devices less than satisfactory, particularly for applications with demanding performance requirements. For example, such devices commonly are subject to undesirable drift, especially as a result of variations in ambient temperature. Also, rapidly opening and closing a switch in series with the winding of a transformer causes instability effects, such as ringing and the like, which interfere with the attainment of high performance levels.

SUMMARY OF THE INVENTION

In a preferred embodiment of the invention, to be described hereinbelow in detail, a half-wave signal isolator is provided wherein capacitor means are connected to the signal transformer to form an LC tank circuit resonant at a frequency close to the frequency of operation of the modulate/demodulate switch circuitry. During the period while the switches are closed, the current in the transformer winding will ramp linearly (in a direction depending upon the input signal polarity), and during the switch-open period the transformer current will follow a cosine curve in a direction opposite to that of the linear ramp. At each on/off and off/on transition of the switches, the ramp wave current and the cosine wave current join smoothly. Thus the transformer current, and the flux in the transformer core, are effectively controlled so as to minimize instability effects which otherwise would interfere with high performance operation of the instrument.

Accordingly, it is a principal object of this invention to provide an improved signal isolator of the half-wave type. It is a specific object of the invention to provide means for avoiding instability effects caused by rapidly opening and closing a modulate/demodulate switch in series with the coupling transformer of a half-wave isolator. Other objects, aspects and advantages of the invention will in part be pointed out in, and in part apparent from, the following detailed description of a preferred embodiment of the invention, considered together with the accompanying drawings.

BRIEF DESCRIPTION OF THE DRAWINGS

FIG. 3 is a detailed schematic diagram of a preferred signal isolator in accordance with the invention.

DESCRIPTION OF THE PREFERRED EMBODIMENT

Figure 1:
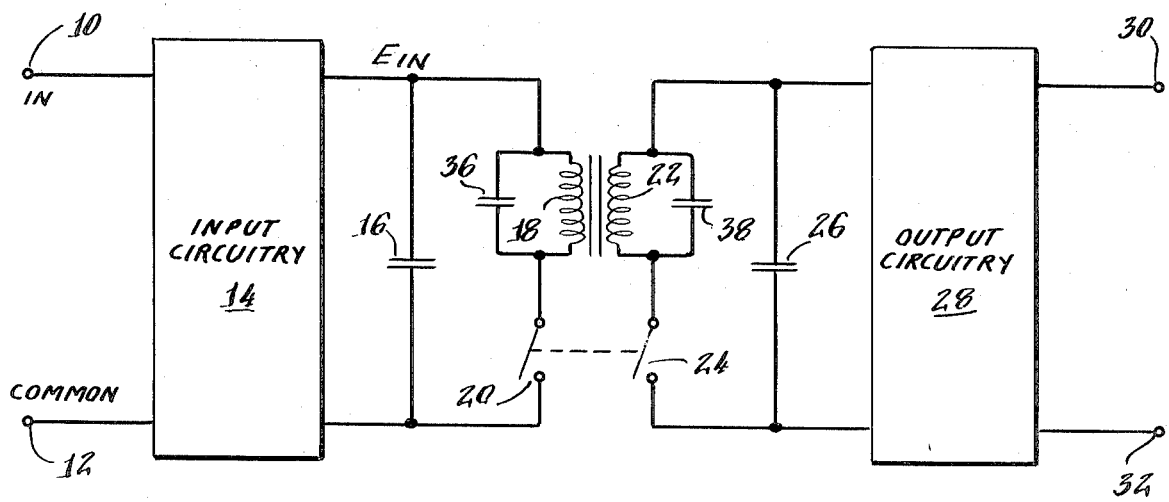
FIG. 1 is a simplified schematic diagram, partly in block format, of an isolator in accordance with the invention.

Referring now to FIG. 1, a half-wave signal isolator in accordance with this invention includes a pair of terminals 10, 12 to receive a d-c input signal. (Although this signal is referred to as d-c, it will be understood that this term is intended also to encompass signals in the audio range or slightly higher.) The input signal is applied first to input circuitry generally indicated at 14, and which may, for example, comprise conventional circuitry including elements such as filters, amplifiers, and so on, adapted to produce a corresponding voltage signal designated as $E_{in}$. This voltage is applied to a reservoir capacitor 16, providing a relatively large storage capacity to minimize fluctuations in the voltage level during operation of the modulator circuit to be described.

The voltage $E_{in}$ is connected to a modulator circuit comprising a transformer primary winding 18 in series with a switch 20. (Although this switch is illustrated as a mechanical device, in the preferred embodiment it would actually be an electronic switch.) The transformer secondary 22 is similarly connected in series with a synchronized demodulator switch 24, and to a second reservoir capacitor 26 which recovers an output voltage level corresponding to $E_{in}$. This output voltage is applied to output circuitry generally indicated at 28 which may for example include known elements such as a filter and an amplifier, and which produces a d-c output signal at the output terminals 30, 32.

In accordance with the present invention, the transformer windings 18 and 22 are provided with resonating capacitors 36, 38 connected in parallel with the respective transformer windings. These capacitors and associated windings thus form a resonant LC tank circuit. The capacity values are selected so that the resonant frequency is approximately equal to the frequency of operation of the switches 20, 24.

Figure 2A:
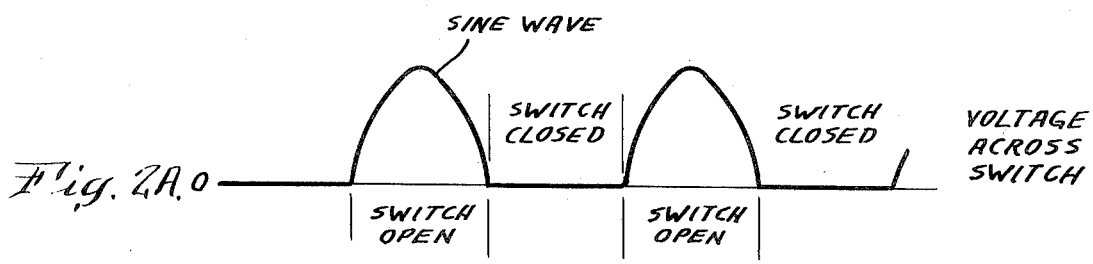
FIGS. 2A, 2B and 2C are curves illustrating principles of the invention.

The operation of the modulator/demodulator circuitry will be explained by reference to the graphs of FIGS. 2A, 2B and 2C which show voltage and current waves for a steady-state condition. As shown in FIG. 2A, the voltage across the switch will be zero during the half-cycles that the switch is closed. During the intervening switch-open periods, however, the resonance of the LC tank circuitry will cause the voltage across the switch to follow a sine curve, reaching a peak voltage of about 3 times the input voltage $E_{in}$. (The voltage across the transformer winding during this switch-open half-cycle will be the inverse of the curve shown in FIG. 2A, offset by the voltage $E_{in}$ across the reservoir capacitor 16.) The voltage across the switch will have returned to zero by the end of each switch-open half-cycle, because the LC tank is resonated at (approximately) the frequency of switch operation.

Figure 2B:

Referring now to FIG. 2B, the current through the switch will of course be zero during the switch-open half-cycles. During the switch-closed half-cycle, this voltage will ramp from a negative value (for positive $E_{in}$), through zero, to a positive value. The positive part of the ramp wave will be slightly greater than the negative part, representing the current flow needed to supply the small losses of the isolator circuitry.

Figure 2C:
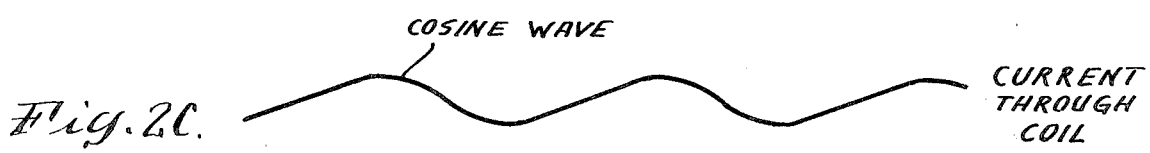

As shown in FIG. 2C, during the switch-closed half-cycle, the current in the transformer winding will ramp positively, as a result of the inductance of the transformer winding with the fixed-value d-c voltage $E_{in}$ applied thereto. When the switch opens at the start of the next half-cycle, the current in the winding will be controlled, as a result of the resonant character of the LC circuitry, to follow a cosine curve returning back to the original level of the ramp current in the switch-closed half-cycle.

The timing of the resonant circuits is set at a frequency providing for smooth transitions between ramp curve and cosine curve. In the preferred embodiment, the switch-open half-cycle is slightly greater than 180°, to assure that the ends of the cosine curve will be aligned with the adjoining ends of the ramp curve, in FIG. 2C. Thus the flux in the transformer core is effectively brought under control, and prevented from causing harmful results from any form of instability.

FIG. 3 shows the circuit details of a commercial isolator embodying the present invention. It will be seen that the switches 20 and 24 are formed by transistor pairs Q1, Q2; Q3, Q4, driven by control signals from drive windings 40, 42 on a separate transformer 44. An oscillator 46 is coupled to a primary winding 48 of this transformer 44 to supply synchronized switch drive signals to windings 40, 42. The transformer 44 also includes power windings 50, 52 which are coupled to respective rectifier circuits 54, 56 for developing d-c operating voltages for input and output amplifiers 58, 60. The isolator input circuitry includes a gain terminal 62 to provide for connection of a gain resistor (not shown) between that terminal and the common terminal 12. The overall gain of the isolator will be determined by the ratio of such gain resistor to the value of a feedback resistor 64 of the input amplifier 58.

Although a specific preferred embodiment of this invention has been described hereinabove in detail, it is desired to emphasize that this has been for the purpose of illustrating the invention, and should not be considered as necessarily limitative of the invention, it being understood that many modifications can be made by those skilled in the art while still practicing the invention claimed herein. For example, although resonating capacitors have been shown for both windings of the coupling transformer, it is possible to achieve effective benefits of the present invention by using a single capacitor connected to only one of the windings. Other changes within the scope of the invention will be evident to those of skill in this art.

I claim:

1. In a signal isolator of the half-wave type comprising a coupling transformer having primary and secondary windings; first and second switches connected to said transformer windings, respectively, one of said switches serving to modulate a signal applied to the transformer primary and the other serving to demodulate the signal developed at the secondary of said transformer; and means for driving said switches in synchronism between closed and open states at a relatively high frequency;

that improvement in such signal isolator comprising:
resonating capacitor means coupled to said transformer during the open switch state to form therewith a resonant circuit tuned at least approximately to said frequency and providing controlled transformer current variations during the open switch state with relatively smooth transitions between the open and closed switch states.

2. A signal isolator as in claim 1, wherein said resonating capacitor means comprises first and second capacitors connected in parallel with said primary and secondary windings respectively to form an LC tank circuit resonant at least approximately at said frequency.

3. A signal isolator as in claim 1, including first and second reservoir capacitors coupled to said primary and seondary windings respectively to provide large-capacity signal sources for the signal to be translated.

4. A signal isolator as in claim 1, including an input amplifier providing an intensified signal for said transformer primary winding.

5. A signal isolator as in claim 1, including an output amplifier coupled to said secondary winding to provide a buffered output signal from said isolator.

6. A signal isolator as in claim 1, wherein said resonant circuit is tuned to provide a switch-open state which is slightly longer than one-half cycle of said switch operating frequency.

* * * * *